United States Patent [19]

Burton

[11] 4,008,721
[45] Feb. 22, 1977

[54] TAPE ELECTRODE FOR TRANSMITTING ELECTRICAL SIGNALS THROUGH THE SKIN

[75] Inventor: Charles V. Burton, Wayzata, Minn.
[73] Assignee: Medtronic, Inc., Minneapolis, Minn.
[22] Filed: Apr. 14, 1975
[21] Appl. No.: 567,612
[52] U.S. Cl. .............................................. 128/418
[51] Int. Cl.² .......................................... A61N 1/04
[58] Field of Search ...... 128/2.06 E, 2.1 E, DIG. 4, 128/404, 417, 418

[56] References Cited

UNITED STATES PATENTS

| | | | |
|---|---|---|---|
| 1,889,272 | 11/1932 | Zerne | 128/418 |
| 3,426,746 | 2/1969 | Seamans, Jr. | 128/2.06 E |
| 3,547,105 | 12/1970 | Paine | 128/2.06 E |
| 3,565,059 | 2/1971 | Hauser | 128/2.06 E |
| 3,607,788 | 9/1971 | Adolph | 128/418 |
| 3,812,861 | 5/1974 | Peters | 128/418 |
| 3,911,906 | 10/1975 | Reinhold, Jr. | 128/2.06 E |

FOREIGN PATENTS OR APPLICATIONS

| 1,965,195 | 7/1971 | Germany | 128/2.06 E |
|---|---|---|---|

Primary Examiner—Robert W. Michell
Assistant Examiner—Lee S. Cohen
Attorney, Agent, or Firm—Schroeder Siegfried Ryan & Vidas

[57] ABSTRACT

A tape form electrode is provided which is usable for transmission of electrical signals into the human body through the skin. The electrode is of a construction so that it can be applied to the skin to secure good electrical contact therewith and remain in place for many days despite normal movement and the normal activities of the subject such as perspiring, and washing. The construction utilizes a porous backing material which has an adhesive layer on one side thereof and over the adhesive layer a second layer which has incorporate therein a quantity of finely divided silver metal. The composition construction is of a thickness and selection of materials such that it readily "breaths" thereby permitting escape of normal amounts of perspiration from the skin of the subject. The adhesive is normally "dry" and is activated at the time of application by a suitable solvent.

11 Claims, 4 Drawing Figures

TAPE ELECTRODE FOR TRANSMITTING ELECTRICAL SIGNALS THROUGH THE SKIN

The present invention is directed to electrodes for application to the outer layer of skin of the human body, and is more specifically directed to such electrodes which are intended to be used as transmission electrodes for injecting significant electrical energy into the human body rather than as mere monitoring electrodes. The current levels in monitoring electrodes is low enough that conductive jellies and the like have been widely used in monitoring electrodes that are on the market. Such jelly type electrodes are less desirable for a number of reasons than the electrodes of the present invention.

An electrode for use on the human skin that is intended to be used for the introduction of electrical energy into the human body desirably would meet a number of goals. Among these would be that the electrode would be one readily handleable by a lay person so that no special skills are involved in its application and use. Not only must it be readily handleable by a lay person, but it is desirably one which has a minimum of care required in its handling and does not produce any mess such as is encountered with the use of conductive jellies. The desirable skin electrode also is one which can be applied to the skin to provide good electrical contact for relatively high powered transmission compared to monitoring electrodes and which can be left in place for many days while the subject wearing the electrode goes about normal activities. In order to be relatively semi-permanently affixed to the skin of the subject, the electrode should be one which has characteristics which strongly discourage the growth of any bacterial or other micro-organisms between the region between the electrode and the skin. Because of the intended relatively high power transmission into the skin of the subject, it is important that the conductivity across the electrode be high enough so as to distribute such a current load over a relatively broad area of skin. This also necessitates a means of electrode lead contact that does not provide local "hot" spots that burn the skin of the subject. Of course, when prolonged application of an electrode is intended, the materials involved in the total electrode usage must be ones which are non-allergenic to the skin of a great majority of patients. A further important requirement of a desirable electrode is that it be low in cost.

In accordance with the present invention, each of the above desirable criteria is accomplished. The electrode of the invention is of simplicity in its construction and its use on the human body. It can be affixed to the skin of a subject readily. Also in accordance with the invention a means of making external lead contact thereto is provided that eliminates the problem of hot spot areas. The electrode is capable of long duration contact with the skin of the subject without causing any allergenic or other adverse reactions on most skins. It can be left on the skin of the subject for long periods of time without loosening and in the event a slight loosening occurs, the electrode can be readily reaffixed to the skin without complete removal therefrom.

The invention will now be described in greater detail with reference to the accompanying drawings wherein.

Figure 1:
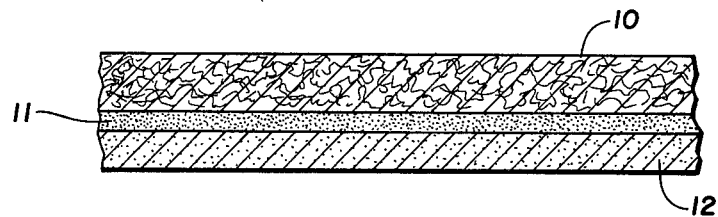
FIG. 1 is a side cross sectional view of a tape form electrode in accordance with the present invention.

Referring first to FIG. 1, there is illustrated in cross sectional and enlarged view for purposes of illustration a tape electrode in accordance with the present invention. The tape electrode consists of a backing material 10 onto which the active materials forming the electrode are applied. The backing material 10 is desirably of a thin, flexible porous cloth like material through which water in either gas or liquid form can pass. The passage of water through this material is the essential requirement in order that moisture that is generated by the skin can have a path for exit so as to avoid any lifting of the tape electrode from the skin under the prolonged usage. Naturally, the backing material 10 must be of a type that is not water soluble. It has been found that a non-woven rayon fiber material is satisfactory for the purpose.

Joined to the tape member 10 on one side thereof is a layer 11 of an adhesive material. While several choices of adhesive material are suitable, it has been found that an acrylic adhesive material are suitable, it has been found that an acrylic copolymer adhesive such as is used in medical tapes is good for this purpose. Layer 11 should be as thin as possible while still providing a total coverage of the one surface of material 10. The function of this adhesive layer is to provide a substrate for application for the active electrode material thereto. Acrylic copolymers when in thin layers have proven to be relatively permeable to moisture and permit the exit of any perspiration materials that are generated by the skin under normal usage. By thin is meant that layer 11 would be just thick enough to provide a sealing function for the surface of backing 10. The actual thickness of the adhesive extending beyond the fabric of backing 10 may be as little a 1 mil.

Layer 11 may be eliminated and layer 12 applied directly to backing 10. However, this is a less desirable construction as it utilizes more of the expensive silver containing material of layer 12, to be described, than is the case when layer 11 is present.

Coated over the surface of layer 11 is a layer 12 which has the electrically active portions of the invention. Layer 12 is a mixture of an adhesive material that is blended with a quantity of silver metal to make the adhesive layer 12 conductive. The quantity of silver metal that must be incorporated within the adhesive of layer 12 may be varied over relatively broad limits. For the sake of economy it is desirable to keep the amount of silver being utilized to as low a level as is possible. This can be accomplished by making the particles of silver metal very small and blending them into the adhesive. A suitable adhesive for the purpose is an acrylic copolymer of the same type as that described in layer 11. One suitable such acrylic polymer is a material available from National Starch Company under their designation resin 30–1289. This material is a vinyl acrylic copolymer in an organic solvent.

The copolymer is blended with a quantity of finely divided silver metal. Silver metal is preferred for its bacterial activity although other skin compatable metal powders like gold or the platinum metals can be used.

The silver metal can be conveniently obtained from Handy and Harmon under their designation Silflake 135. The silver from this source is in a flake form so that it retains it metallic appearance. Such a metallic appearance is helpful to the user thereof to identify that it is a metallic material. A suitable blend includes approximately 1,000 grams of the silver is blended with 300 grams of the copolymer material to make the material which is applied as a coating 12. Higher amount of silver relative to copolymer may be utilized in forming layer 12. The higher quantity of silver is desirable in reducing the volume resistivity of the finished coating 12, but results in a commensurately higher cost per unit area of electrode. Somewhat lower quantities of silver can be utilized with commensuately increased volume resistivity. In the quantities indicated, the volume resistivity will be less than one ohm-centimeters. With the quantity of silver that is given above, the composite material forming layer 12 will be in a essentially non-tacking condition. This is desirable for ready rolling and storage of the material. In applying layer 12 over layer 11, it is desirable to fluidize the silver-acrylic copolymer by incorporation therein of a quantity of a suitable solvent such as toluene and acetone. Following the coating operation the solvent readily evaporates to leave the finished material. The thickness of layer 12 should be as low as is possible while retaining electrical continuity across the tape surface. By so doing not only is cost reduced, but more importantly the layer 12 is more readily permeable to moisture with declining thickness. For long term application to the skin this is a critical factor. Desirably, layer 12 is less than 5 mils in thickness and preferably 2 – 3 mils.

A completed tape can be made in the lengths desired for ultimate distribution to the users. When a tape is made, one may conveniently place a liner of a silicone or polyethylene coated paper as a protection to the coated surface until it is desired to actually use a section of the tape as an electrode. Alternatively, the outer face of backing 10 may be treated so as to make it non-adhereable to layer 12 when the finish tape is coiled on itself. In this latter case, the treatment must be such that moisture permeability is not lost by such treatment.

Figure 2:
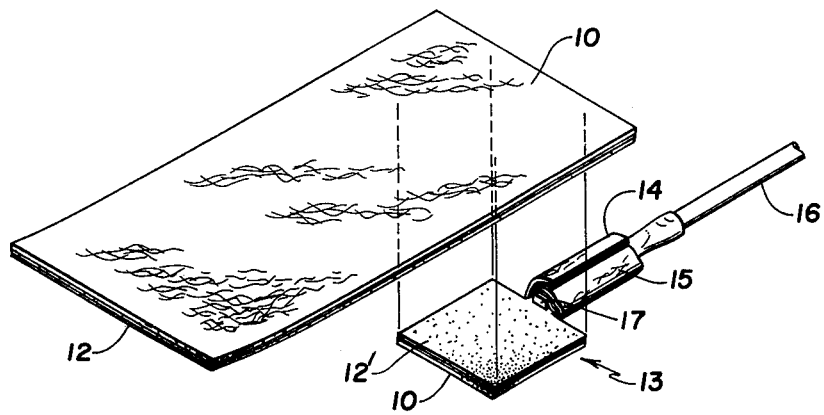
FIG. 2 is a perspective view of an electrode lead and tape in accordance with the invention in exploded view.

Referring now to FIG. 2 there is illustrated in a perspective view a tape member as described in FIG. 1 and a means for applying an electrode thereto prior to the application to the skin of the subject. The electrode contact means comprises a small piece of tape of the same type as that previously described. The electrode connection is generally designated as 13.

The connector 13 of FIG. 2 comprises a small rectangular piece of tape which may be of a construction as shown in FIG. 1 which has been slit part way through on opposite sides thereof adjacent one end as illustrated to provide tabs 14 and 15. An insulated lead wire 16 having a bare metal exposed end thereon 17 is inserted so that the metallic end 17 is in direct physical contact with layer 12' between the tab ends 14 and 15. These tab ends are then wrapped around the metallic end as shown and bonded thereto by ordinary pressure or with the aid of a quantity of solvent. This makes a direct electrical contact not only with the tabs 14 and 15 but also with the balance of the layer 12'. Layer 12' which includes a contact adhesive readily can be joined to layer 12 of the tape electrode member by placing the two layers 12 and 12' in physical contact with one another. Thus, complete electrical contact is achieved throughout the surface of the tape to be applied to the subject skin and there are no localized hot spots that will arise due to a contact point of a narrow wire electrode.

Figure 4:
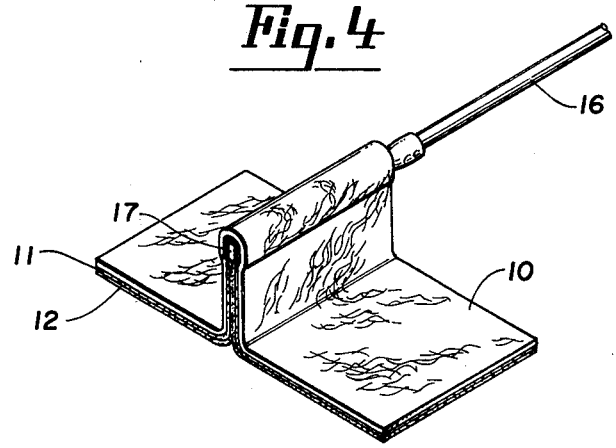

FIG. 4 illustrates an alternate means of making electrical connection to a tape electrode in accordance with the invention. In this instance, a strip of tape electrode is described in FIG. 1 has the lead member 16 bare end 17 pressed to an intermediate portion between the ends thereof. Portions of the layer 12 are pressed together to envelope end 17 as shown with the free ends of the tape electrode available for contact to the skin. An upstanding loop of tape isolates lead 17 from direct contact to the skin.

Figure 3:
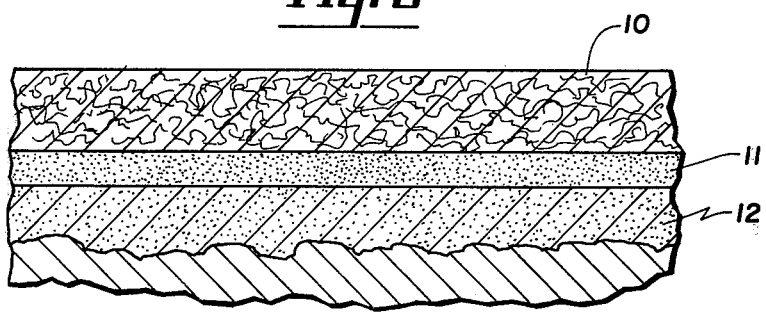
FIG. 3 is a cross sectional and schematic illustration of an electrode in accordance with the invention affixed to the skin; and, FIG. 4 is an alternative form of applying a lead to the tape electrode.

In actual use, the tape and electrode assembly of the invention are applied as follows: the subject determines the area of skin to which he wishes to apply an electrode and cleans it in the ordinary manner, washing excess body oils from the surface of the skin. A tape of suitable size is cut from a spool and an electrode assembly either previously made or fabricated at the time of usage in accordance with the description given with FIGS. 2 or 4 is joined in the manner previously described to the tape to be applied to the subject's skin. The skin of the subject is then either coated with a layer of a skin compatable solvent for the adhesive of layer 12 such as acetone or a low molecular weight alcohol and facing 12 of the tape is placed against this liquid layer. The function of the solvent is to partially dissolve layer 12 to give it a high tack and wetting capability to the human skin. In this condition, the electrode material 12 readily penetrates into the intricacies of the human skin as is generally illustrated in FIG. 3 to provide the intimacy of physical contact not available with mere contact adhesives of some of the prior art.

As a preferred method of applying an electrode, the electrode with face 12 toward the skin is pressed on to the skin of the subject. Little, if any, adhesion results in this step. Then the solvent, such as acetone or a low molecular weight alcohol is applied through the back 10 of the tape, penetrates down through the layers 10, and 11 and partially solubilizes layer 12 bringing about the same type of intimate skin contact as illustrated in FIG. 3. The solvent having a low boiling point readily evaporates from the tape electrode resulting in a semi-permanent bond of the electrode to the skin. Should the applied tape show undesired signs of loosening, use of a drop of solvent through backing 10 readily re-adheres the tape to the skin.

An electrode so constructed and applied to the skin provides all of the advantages which were initially set forth in the specification above. The combination of a water insoluble material that is of very low thickness permits the transmission of water vapor thereacross so that it does not have any significant tendency to loosen or flake off under prolonged exposure. The fact that the adhesive is water insoluble permits its use under conditions where the subject is bathing and is otherwise exposing the exterior parts of the electrode to normal daily conditions.

Once the purpose for which the electrode has been attached is no longer required, the electrode may be readily removed. A user merely grips and peels the electrode off from the skin. If desired, any residual amount of adhesive and silver which is retained on the skin due to intricacies of the skin surface can be loosened and washed free by use of the same solvent that is utilized in softening and solubilizing in the instance of applying the electrode.

What I claim is:

1. A tape electrode for prolonged adhesion to the epidermal layer of skin of a human, and re-adhereable should it loosen in use without removal by application of a non-aqueous solvent to the adhesive free side thereof comprising:
   a. a highly porous tape substrate;
   b. a conductive coating on one surface of said substrate, said conductive coating including a mixture of skin compatible metal particles blended into a water insoluble, low-tack adhesive matrix in an amount sufficient to provide electrical continuity between the metal particles, said adhesive matrix being a non-toxic, non-irritating and non-allergenic polymer that is at least partially soluble in a volatile organic solvent, the thickness of said adhesive matrix coating being such that water vapor generated at the surface of the skin readily permeates through said coating layer and tape substrate; and
   c. a lead wire electrically joined to the conductive coating and in isolation from the surface of said conductive coating adapted to be placed in contact with the skin, said lead wire being enveloped between two layers of the tape substrate with the conductive coatings thereof against each other and said lead wire.

2. A tape electrode in accordance with claim 1 wherein said metal particles are silver.

3. A tape electrode in accordance with claim 2 wherein said conductive coating has a volume resistivity of less than one ohm-cm.

4. A tape electrode in accordance with claim 1 wherein the adhesive matrix is an acrylic copolymer and said coating is less than 5 mils in thickness.

5. A tape electrode in accordance with claim 4 wherein said coating has a volume resistivity of less than one ohm-cm.

6. A tape electrode in accordance with claim 1 wherein said substrate has a non-conducting moisture permeable adhesive layer intermediate said substrate and said conductive coating.

7. A tape electrode for prolonged adhesion to the epidermal layer of skin of a human, and re-adherable should it loosen in use without removal by application of a non-aqueous solvent to the adhesive free side thereof comprising: A highly porous flexible tape substrate; and an electrically conductive coating on one surface of said substrate, said conductive coating including a mixture of skin compatible metal particles blended into a water insoluble, and at least partially volatile organic solvent soluble, low-tack adhesive matrix in an amount sufficient to provide electrical continuity between the metal particles, and to produce a coating that is essentially tack free, said adhesive matrix being an acrylic copolymer and said coating being less than 5 mils in thickness, said thickness of said adhesive matrix coating being such that water vapor generated at the surface of the skin readily permeates through said coating layer and tape substrate.

8. A tape electrode in ccordance with claim 7 wherin said coating of metal particles and adhesive matrix is 2–3 mils in thickness.

9. A tape electrode in accordance with claim 8 wherein the metal particles are silver and the conductive coating has a volume resistivity of less than 1 ohm — centimeter.

10. A tape electrode in accordance with claim 9 wherein the substrate has a metal particle free acrylic copolymer adhesive layer intermediate said substrate and said conductive coating.

11. A tape electrode for prolonged adhesion to the epidermal layer of skin of a human, and re-adherable should it loosen in use without removal by application of a non-aqueous solvent to the adhesive free side thereof comprising: a highly porous flexible tape substrate; and an electrically conductive coating on one surface of said substrate, said conductive coating including a mixture of skin compatible metal particles blended into a water insoluble, and at least partially volatile organic solvent soluble, low-tack adhesive matrix in an amount sufficient to provide electrical continuity between the metal particles and to produce a coating that is essentially tack free, said adhesive matrix being an acrylic copolymer and said coating being less than 5 mils in thickness, said thickness of said adhesive matrix coating being such that water vapor generated at the surface of the skin readily permeates through said coating layer and tape substrate; said flexible tape electrode being adapted to have a portion thereof adhered to and surround a lead wire to provide disbursed electrical continuity to the entire exposed surface of the tape while electrically and physically isolating the lead from proximity to the skin of the user.

* * * * *

UNITED STATES PATENT OFFICE
CERTIFICATE OF CORRECTION

PATENT NO. : 4,008,721
DATED : February 22, 1977
INVENTOR(S) : Charles V. Burton It is certified that error appears in the above-identified patent and that said Letters Patent are hereby corrected as shown below:

Column 2, lines 28-29, after "acrylic", delete "adhesive material are suitable, it has been found that an acrylic".

Signed and Sealed this

Thirty-first Day of May 1977

[SEAL]

Attest:

RUTH C. MASON
*Attesting Officer*

C. MARSHALL DANN
*Commissioner of Patents and Trademarks*